United States Patent
Liang et al.

(10) Patent No.: US 11,565,152 B2
(45) Date of Patent: Jan. 31, 2023

(54) EXERCISE SENSING METHOD, APPARATUS AND SYSTEM

(71) Applicant: Industrial Technology Research Institute, Hsinchu (TW)

(72) Inventors: Min-Hsiung Liang, Taichung (TW); Yun-Yi Huang, Pingtung County (TW); Tzu-Yang Ting, Taipei (TW); Yu-Jhen Yang, Hsinchu (TW); Tzu-Hao Yu, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 372 days.

(21) Appl. No.: 16/843,849

(22) Filed: Apr. 8, 2020

(65) Prior Publication Data
US 2021/0197023 A1 Jul. 1, 2021

(30) Foreign Application Priority Data
Dec. 27, 2019 (TW) .................. 108147977

(51) Int. Cl.
*A63B 24/00* (2006.01)
*G16H 20/30* (2018.01)

(52) U.S. Cl.
CPC .......... *A63B 24/0062* (2013.01); *A63B 24/00* (2013.01); *A63B 24/0087* (2013.01);
(Continued)

(58) Field of Classification Search
CPC . A63B 24/0062; A63B 24/00; A63B 24/0087; A63B 2024/0068;
(Continued)

(56) References Cited

U.S. PATENT DOCUMENTS

| | | | |
|---|---|---|---|
| 8,398,546 B2 | 3/2013 | Pacione et al. | |
| 8,500,604 B2 * | 8/2013 | Srinivasan | A63B 24/0062 482/3 |

(Continued)

FOREIGN PATENT DOCUMENTS

| | | |
|---|---|---|
| CN | 103191557 | 7/2013 |
| CN | 104208865 | 12/2014 |

(Continued)

OTHER PUBLICATIONS

"Office Action of Taiwan Counterpart Application", dated Jun. 1, 2020, p. 1-p. 10.
(Continued)

*Primary Examiner* — Allen Chan
(74) *Attorney, Agent, or Firm* — JCIPRNET (57) ABSTRACT

An exercise sensing method, an exercise sensing apparatus and an exercise sensing system are provided. The exercise sensing system includes a computing device, a storage device and at least one biophysical quantity sensor disposed on at least one muscle portion of a user. In the method, a current muscle strength of the muscle portion when the user performs an exercise is monitored by the biophysical quantity sensor. An exercise history of the user is accessed to obtain a muscle strength reference value of the muscle portion when the user previously performed the exercise. The current muscle strength is compared with the muscle strength reference value so as to adjust an exercise intensity of the exercise.

12 Claims, 6 Drawing Sheets

(52) U.S. Cl.
CPC ...... G16H 20/30 (2018.01); *A63B 2024/0068* (2013.01); *A63B 2024/0093* (2013.01); *A63B 2230/062* (2013.01); *A63B 2230/605* (2013.01)

(58) Field of Classification Search
CPC ...... A63B 2024/0093; A63B 2230/062; A63B 2230/605; G16H 20/30
USPC .......................................... 73/379.01; 482/8
See application file for complete search history.

(56) References Cited

U.S. PATENT DOCUMENTS

| | | | |
|---|---|---|---|
| 9,474,934 B1 * | 10/2016 | Krueger | ............... A61B 5/4872 |
| 9,993,688 B2 * | 6/2018 | Siegel | .................... A63B 23/20 |
| 2014/0174174 A1 | 6/2014 | Uehara et al. | |
| 2017/0046108 A1 | 2/2017 | Kang et al. | |
| 2018/0178066 A1 | 6/2018 | Krueger et al. | |
| 2019/0046839 A1 * | 2/2019 | Jang | ........................ A41B 1/08 |

FOREIGN PATENT DOCUMENTS

| | | |
|---|---|---|
| CN | 106709228 | 5/2017 |
| CN | 109716443 | 5/2019 |
| TW | 201532648 | 9/2015 |
| TW | I505228 | 10/2015 |

OTHER PUBLICATIONS

"Office Action of China Counterpart Application", dated Oct. 19, 2021, p. 1-p. 8.

* cited by examiner

EXERCISE SENSING METHOD, APPARATUS AND SYSTEM

CROSS-REFERENCE TO RELATED APPLICATION

This application claims the priority benefit of Taiwan application serial no. 108147977, filed on Dec. 27, 2019. The entirety of the above-mentioned patent application is hereby incorporated by reference herein.

TECHNICAL FIELD

The disclosure relates to a sensing technology and also relates to an exercise sensing method, an exercise sensing apparatus, and an exercise sensing system.

BACKGROUND

Nowadays, exercise is increasingly popular, and it is common for people to take fitness or weight training in health clubs or gyms. However, unless there is onsite coaching, people generally do exercise without professional exercise planning, and they may not be able to adjust the exercise menu based on the past record and the current physical state to improve the exercise performance. In addition, as people switch between different types of training machines, they may not know how to choose the machine and the training cycles to connect with the previous exercise.

If the exercise intensity of the chosen machine and training cycles is too low, the exercise may not bring the ideal result. However, if the exercise intensity is too high, it may overwork the muscle, which not only fails to increase muscle strength but also causes injuries. If the exercise is too intense, it may result in an overly high heart rate and increase the heart load.

SUMMARY

According to an embodiment of the disclosure, an exercise sensing method is provided, which is adapted for an exercise sensing system including a computing device and at least one biophysical quantity sensor. The biophysical quantity sensor is disposed on at least one muscle portion of a user. The exercise sensing method includes: monitoring a current muscle strength of the muscle portion when the user performs an exercise with the biophysical quantity sensor; accessing an exercise history of the user to obtain a muscle strength reference value of the muscle portion when the user previously performed the exercise; and comparing the current muscle strength with the muscle strength reference value to adjust an exercise intensity of the exercise.

According to an embodiment of the disclosure, an exercise sensing system is provided, which includes: at least one biophysical quantity sensor, a storage device, and a computing device. The biophysical quantity sensor is disposed on at least one muscle portion of a user to sense a force exerted by the muscle portion. The storage device is configured to record an exercise history of the user. The computing device is coupled to the biophysical quantity sensor and the storage device, and is configured to monitor a current muscle strength of the muscle portion when the user performs an exercise with the biophysical quantity sensor, access an exercise history of the user from the storage device to obtain a muscle strength reference value of the muscle portion when the user previously performed the exercise, and compare the current muscle strength with the muscle strength reference value to adjust an exercise intensity of the exercise.

According to an embodiment of the disclosure, an exercise sensing apparatus is provided, which includes: a connecting device, a storage device, and a computing device. The connecting device is configured to receive a force exerted by at least one muscle portion of a user monitored by at least one biophysical quantity sensor disposed on the muscle portion. The storage device is configured to record an exercise history of the user. The computing device is coupled to the connecting device and the storage device, and is configured to receive the force exerted by the muscle portion monitored by the biophysical quantity sensor when the user performs an exercise with the connecting device to calculate a current muscle strength of the muscle portion, access the exercise history of the user from the storage device to obtain a muscle strength reference value of the muscle portion when the user previously performed the exercise, and compare the current muscle strength with the muscle strength reference value to adjust an exercise intensity of the exercise.

Several exemplary embodiments accompanied with drawings are described in detail below to further describe the disclosure.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DETAILED DESCRIPTION OF DISCLOSED EMBODIMENTS

An embodiment of the disclosure provides an exercise sensing system integrating current muscle strength and heart rate sensing, which compares the physiological data sensed during the current exercise with historical data to effectively determine the current state of the user's body and adjust the intensity or menu of the subsequent exercise accordingly. Thereby, it helps the user achieve higher exercise effectiveness and avoid exercise injuries. In addition, in an embodiment of the disclosure, a total exertion work of a muscle group corresponding to the combinations of different training machines and training amounts is further calculated, so that when the user needs to adjust the exercise intensity or menu, the user can be instantly provided with a substitute machine and a substitute training amount with equivalent exercise intensity to continue the training.

Figure 1:
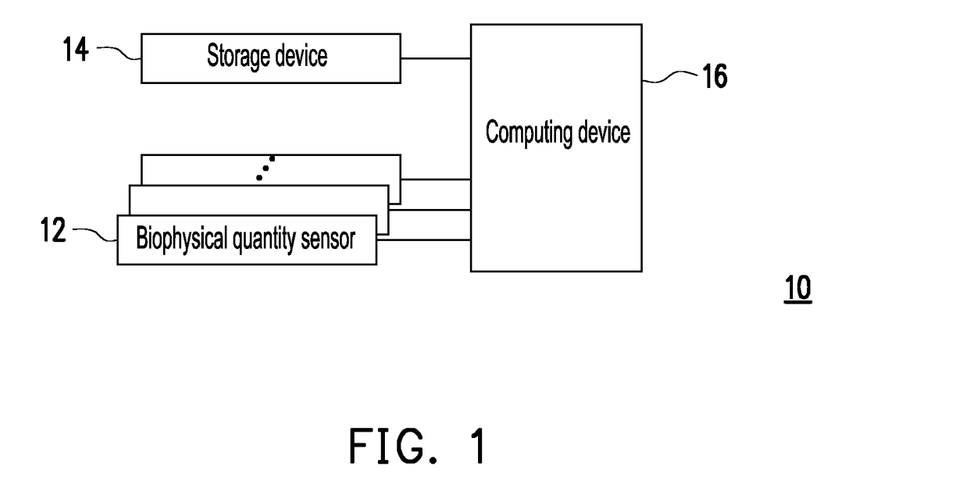
FIG. 1 is a block diagram of an exercise sensing system according to an embodiment of the disclosure.

FIG. 1 is a block diagram of an exercise sensing system according to an embodiment of the disclosure. Referring to FIG. 1, the exercise sensing system 10 of the present embodiment includes at least one biophysical quantity sensor 12, a storage device 14, and a computing device 16. The functions thereof are described as follows.

The biophysical quantity sensor 12 obtains biological movement information using bioelectrical detection, biomagnetic detection or non-electromagnetic physiological parameter detection, and may be a neuromuscular sensor, including: an electromyography signal sensor (EMG sensor), a mechanomyography sensor (MMG sensor), a sonomyography sensor (SMG sensor), etc. The biophysical quantity sensor 12 is implemented in forms such as clothing (for example, coats, tops, pants, skirts, underwear, etc.) that can be worn by the user, accessories (for example, gloves, bracelets, anklets, hats, socks, belts, headbands, cufflinks, etc.), patches, straps, waist pads, knee pads, ankle pads, and shoes, but the disclosure is not limited thereto. The biophysical quantity sensor 12 is disposed on, for example, at least one muscle portion that exerts a force when the user exercises. For example, when the user does a seated rowing exercise, the biophysical quantity sensor 12 may be respectively disposed on the biceps and latissimus dorsi of the user to detect the force exerted. When the user does a standing cable rowing exercise, the biophysical quantity sensor 12 may be respectively disposed on the deltoid and trapezius of the user to detect the force exerted.

The storage device 14 is, for example, any type of fixed or movable random access memory (RAM), read-only memory (ROM), flash memory, hard disk, similar devices, or a combination of the foregoing and is configured to store a program to be executed by the computing device 16. In an embodiment, the storage device 14 also records an exercise history of the user.

The computing device 16 is, for example, a central processing unit (CPU), a programmable general-purpose or special-purpose microprocessor, a digital signal processor (DSP), a programmable controller, an application specific integrated circuit (ASIC), other similar devices, or a combination of the foregoing. In the present embodiment, the computing device 16 is coupled to the biophysical quantity sensor 12 and the storage device 14 respectively, and may receive monitoring data from the biophysical quantity sensor 12 and load a computer program from the storage device 14 to execute an exercise sensing method of an embodiment of the disclosure.

In an embodiment, the exercise sensing system 10 may further include a heart rate sensor (not shown) such as a photoplethysmography (PPG) sensor or an electrocardiogram (ECG) sensor, which is, for example, worn or disposed on a portion of the user where the heart rate can be sensed (for example, the heart, wrist, etc.) and is configured to sense a change of the heart rate of the user during exercise to provide a basis for the computing device 16 to adjust the exercise intensity or menu.

In an embodiment, the exercise sensing system 10 may further include a prompt device (not shown) such as a display, a speaker, a light-emitting diode (LED) array, a vibrator, or any combination of the foregoing, which may accept control of the computing device 16 and prompt the user to increase or decrease the exercise intensity or change the machine or training amount by visual, auditory and/or tactile means.

Figure 2:
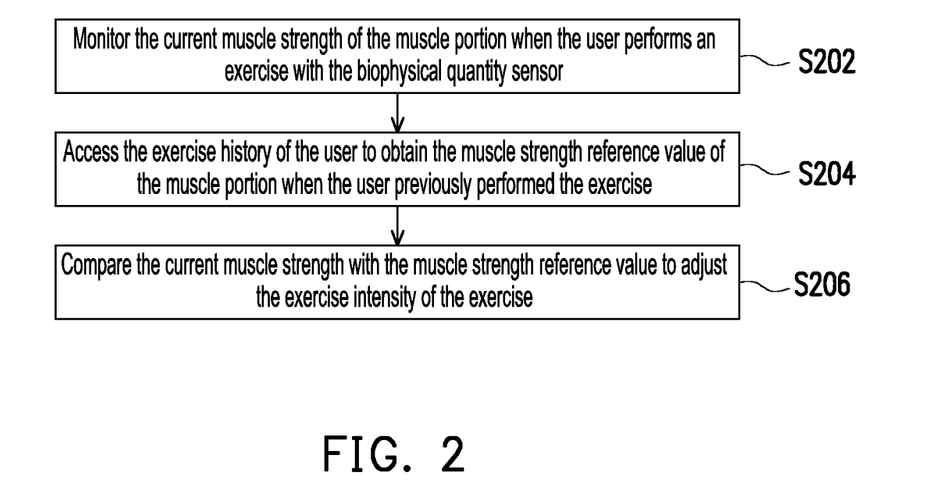
FIG. 2 is a flowchart of an exercise sensing method according to an embodiment of the disclosure.

FIG. 2 is a flowchart of an exercise sensing method according to an embodiment of the disclosure. Referring to FIG. 1 and FIG. 2, the method of the present embodiment is applicable to the exercise sensing system 10 in FIG. 1. The following describes the processes of the exercise sensing method of the present embodiment with the interaction between the elements in the exercise sensing system 10.

First, in Step S202, the computing device 16 uses the biophysical quantity sensor 12 to monitor a current muscle strength of each muscle portion when the user performs an exercise (for example, operating a weight training device). In an embodiment, the computing device 16 monitors a muscle strength intensity of each muscle portion when the user exercises to obtain a muscle strength curve, and calculates a peak value of the muscle strength curve as the current muscle strength of the muscle portion.

During the exercise of the user, the computing device 16 continuously monitors the biophysical quantity of the user with the biophysical quantity sensor 12, and calculates an average signal for a complete cycle. The computing device 16 uses, for example, an integral of an EMG signal V(t) (IEMG) or a root mean square (RMS) of an EMG signal V(t) to obtain the corresponding muscle strength $P1_{PM}$ (IEMG) or $P2_{PM}$ (RMS).

$$\begin{cases} P1_{PM} = \int_0^T V(t)dt \\ P2_{PM} = \sqrt{\dfrac{\int_0^T V(t)^2 dt}{T}} \end{cases}$$

Returning to the flowchart of FIG. 2, in Step S204, the computing device 16 accesses an exercise history of the user from the storage device 14 to obtain a muscle strength reference value of the muscle portion when the user previously performed the exercise. In an embodiment, the muscle strength reference value is the peak value of the muscle strength curve obtained by monitoring the muscle strength intensity of the same muscle portion during the previous exercise. In other embodiments, the muscle strength reference value may also be a maximum value, an average value, a median value, or other statistical values of the peak muscle strength intensity monitored during previous exercises, but the disclosure is not limited thereto.

In Step S206, the computing device 16 compares the current muscle strength with the muscle strength reference value to adjust the exercise intensity of the exercise. In an embodiment, the computing device 16 calculates a change percentage of the current muscle strength relative to the muscle strength reference value, and adjusts the exercise menu according to the change percentage to increase or decrease the exercise intensity of the exercise.

Figure 3:
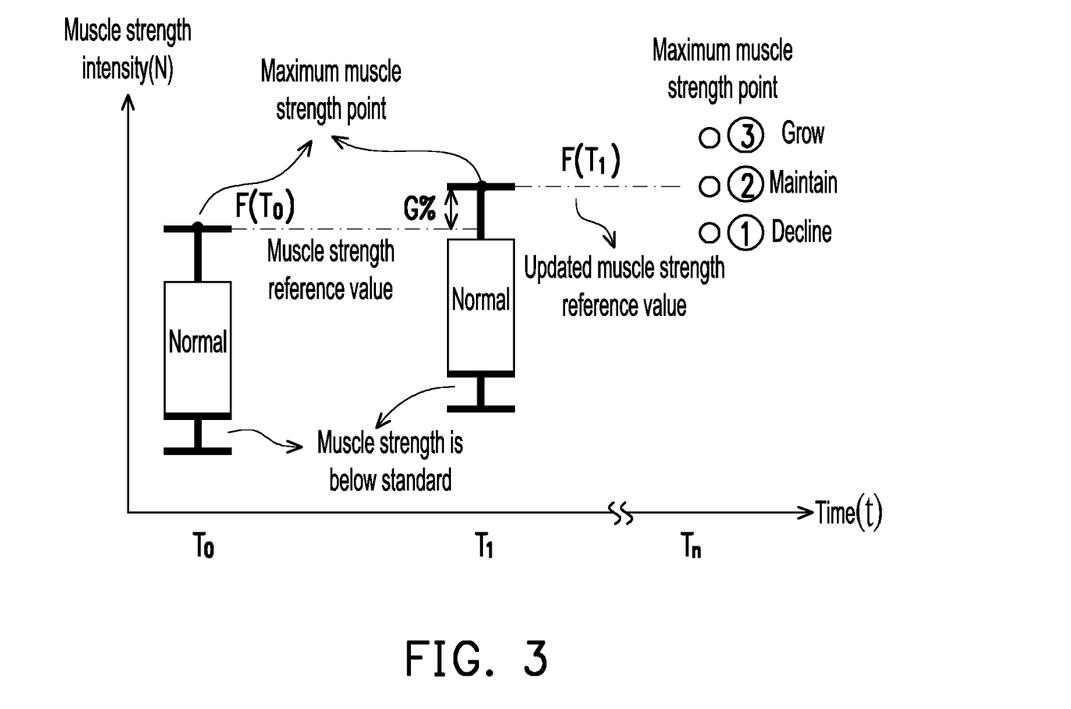
FIG. 3 is an example of an exercise sensing method according to an embodiment of the disclosure.

FIG. 3 is an example of the exercise sensing method according to an embodiment of the disclosure. Referring to FIG. 3, in the present embodiment, for example, the currently monitored current muscle strength $F(T_1)$ is compared with the muscle strength reference value $F(T_0)$ obtained previously to obtain the muscle strength growth/decline percentage G(%), and the formula is as follows.

$$G = 100 \times [F(T_1) - F(T_0)]/F(T_0)$$

Thereafter, the exercise intensity may be adjusted using the G value according to an exercise intensity adjustment table (for example, Table 1 below). If the G value is positive (that is, the maximum muscle strength point grows), it represents an increase in muscle strength intensity, and the exercise intensity may be increased according to the corresponding field in the exercise intensity adjustment table (for example, G=10% corresponds to $Y_{10}$% in Table 1). Conversely, if the G value is negative (that is, the maximum muscle strength point declines), it represents a decline in muscle strength intensity, and the exercise intensity needs to be decreased. After the exercise intensity is adjusted, the monitored current muscle strength $F(T_1)$ may be recorded as an updated muscle strength reference value to serve as the reference for the next evaluation of the muscle strength intensity.

TABLE 1

| G % | Exercise intensity |
|---|---|
| +X % | Increase $Y_X$ % |
| 0% | Increase $Y_0$ % |
| −Z % | Decrease $Y_{-Z}$ % |

Figure 4:
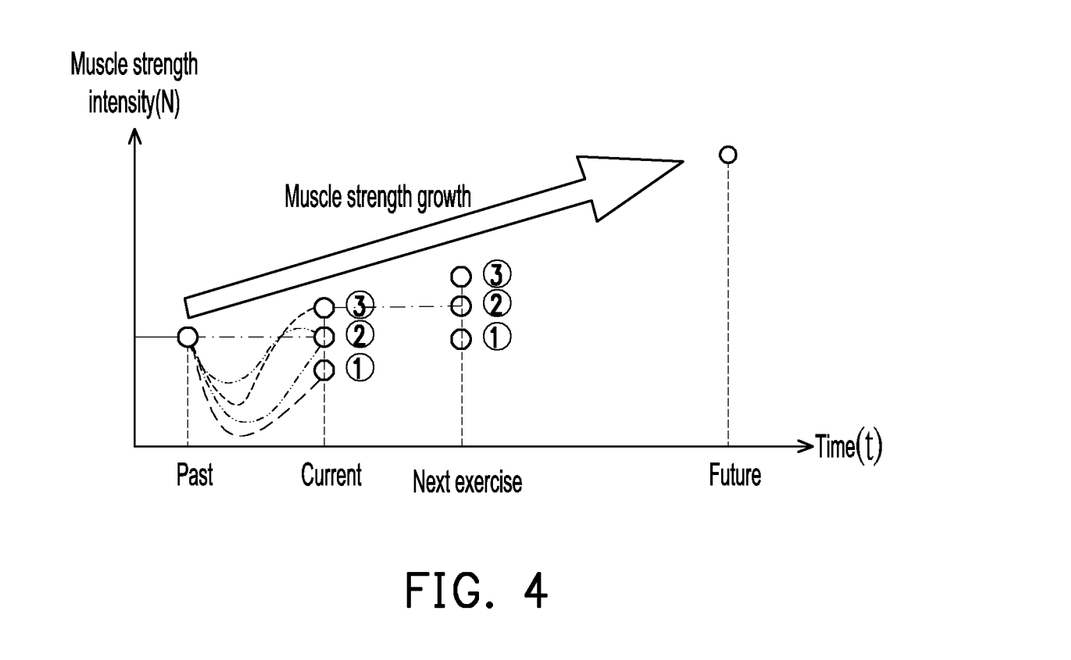
FIG. 4 is a diagram of a muscle strength growth curve according to an embodiment of the disclosure.

FIG. 4 is a diagram of a muscle strength growth curve according to an embodiment of the disclosure. Referring to FIG. 4, in the present embodiment, the muscle strength intensity monitored in the past is taken as the muscle strength reference value for comparison with the current muscle strength of the user currently monitored.

If the current muscle strength is lower than the muscle strength reference value (zone ① shown in the figure), it represents that the user has insufficient rest time or the exercise intensity is too high. In such a case, the user may be advised to decrease the exercise intensity.

If the current muscle strength is equal to the muscle strength reference value (zone ② shown in the figure), it represents that the muscle strength of the user has not grown. There are two possible reasons for this situation. The first one may be that the muscle strength has not been restored to the overcompensation zone due to insufficient rest time; the second one may be that the muscle strength has declined to the original state because the rest time is too long. Therefore, if the exercise intensity of the menu is increased in such a situation, the muscle strength of the user under the first condition will decline to the zone ①. In such a case, the exercise intensity may be lowered to a level lower than the previous exercise intensity, and the muscle strength may grow to the zone ③. For the user under the second condition, after the exercise intensity is increased, the muscle strength may also grow to the zone ③.

Referring to FIG. 4 again, for the next exercise, the currently monitored muscle strength intensity is taken as the muscle strength reference value for comparison with the current muscle strength of the user monitored during the next exercise.

If the current muscle strength is higher than the muscle strength reference value (zone ③ shown in the figure), it represents that the previous exercise intensity is appropriate, but in order to obtain the optimal exercise intensity, the exercise intensity of the menu may be increased gradually. Thereby, in addition to finding the optimal training intensity, it is also possible to further increase the training amount as the muscle strength grows.

According to the present embodiment, with the method described above, the muscle strength intensity of the user during exercise is sensed, and whether the current state of the user meets the requirement of the exercise menu is evaluated so as to adjust the menu instantly for the exercise intensity to match the current state of the user. Thereby, the exercise effectiveness is improved and exercise injuries are avoided.

In an embodiment, the aforementioned muscle strength intensity evaluation may be further combined with heart rate intensity evaluation to reflect the current state of the user so as to adjust the exercise intensity instantly to prevent the exercise amount from exceeding the heart load.

Figure 5:
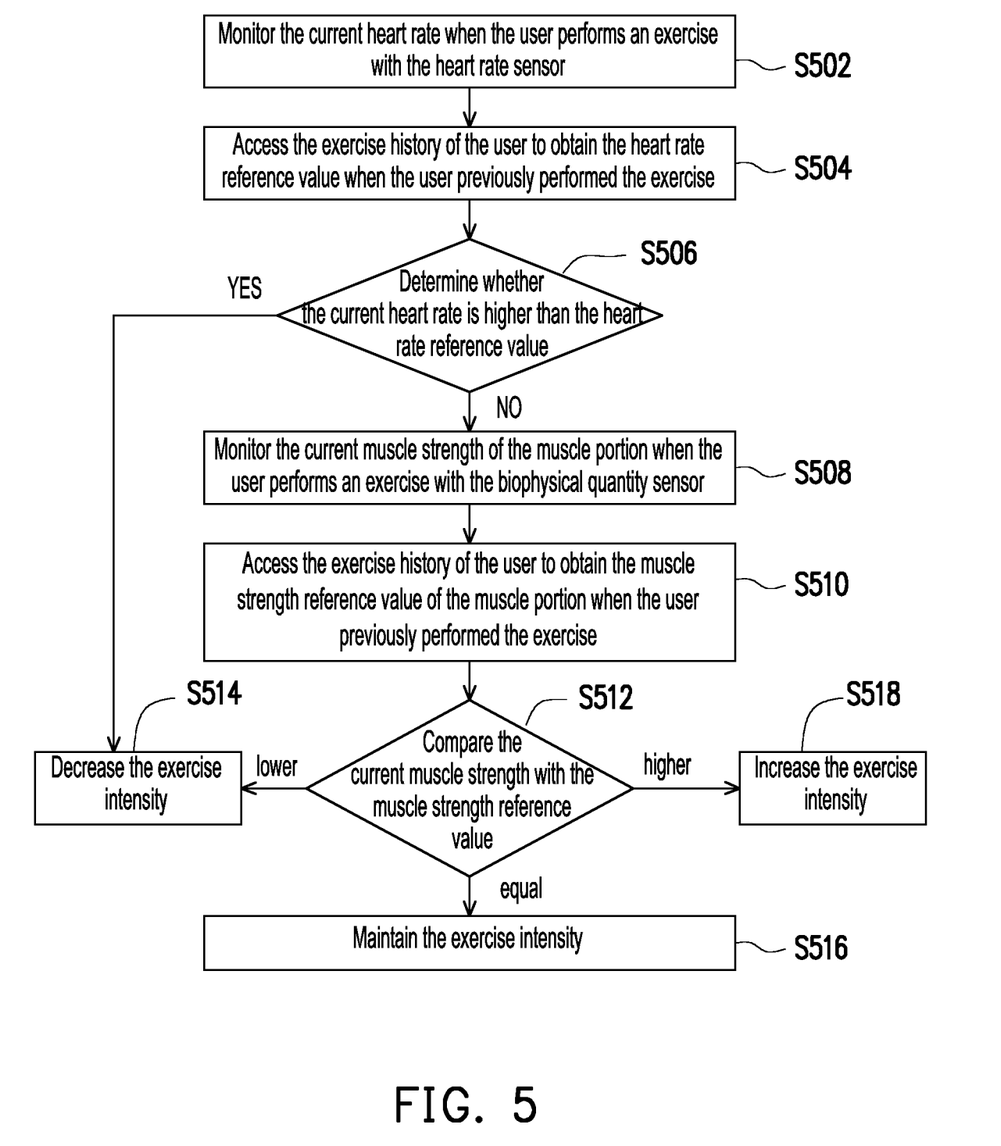
FIG. 5 is a flowchart of an exercise sensing method according to an embodiment of the disclosure.

FIG. 5 is a flowchart of an exercise sensing method according to an embodiment of the disclosure. Referring to FIG. 1 and FIG. 5, the method of the present embodiment is applicable to the exercise sensing system 10 in FIG. 1. The following describes the processes of the exercise sensing method according to the embodiment of the disclosure with the interaction between the elements in the exercise sensing system 10.

First, in Step S502, the computing device 16 uses a heart rate sensor (not shown) to monitor a current heart rate when the user performs an exercise. In Step S504, the computing device 16 accesses an exercise history of the user from the storage device 14 to obtain a heart rate reference value when the user previously performed the exercise for comparison with the monitored current heart rate.

Figure 6:
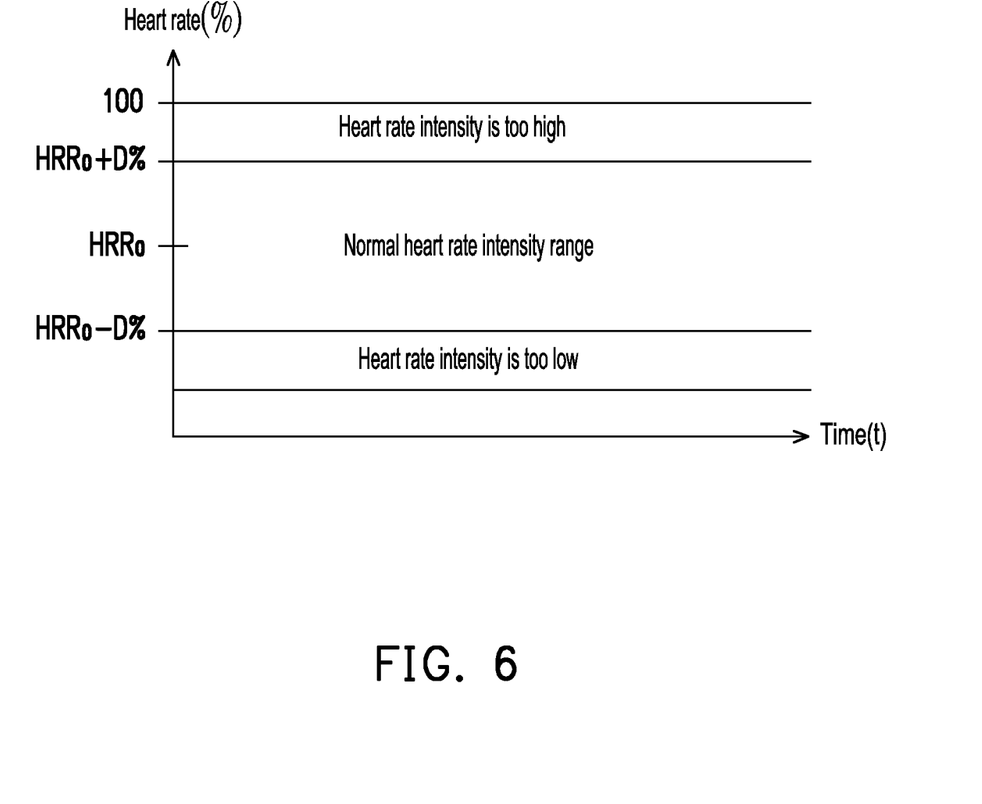
FIG. 6 is an example of an exercise sensing method according to an embodiment of the disclosure.

For example, FIG. 6 is an example of the exercise sensing method according to an embodiment of the disclosure. Referring to FIG. 6, for example, in the present embodiment, the heart rate sensor is turned on when the user starts to exercise to dynamically monitor the current heart rate intensity HR(t) of the user during the exercise so as to obtain a heart rate state curve. In addition, in the present embodiment, the exercise history of the user may also be accessed to obtain a heart rate reference value $HRR_0$ when the user previously performed the exercise, and then a percentage difference D between the current heart rate intensity HR(t) of the user during the exercise and the heart rate reference value $HRR_0$ in the past is calculated. The formula is as follows.

$$D=100\times[HR(t)-HRR_0]/HRR_0$$

In the present embodiment, for example, whether the difference between the current heart rate intensity HR(t) and the heart rate reference value $HRR_0$ falls within a range of +/−D % of the heart rate reference value $HRR_0$ is determined. If the difference between the current heart rate intensity HR(t) and the heart rate reference value $HRR_0$ falls within the range of +/−D % of the heart rate reference value $HRR_0$, it represents that the current heart rate intensity HR(t) falls within a normal heart rate intensity range. In such a case, the current exercise intensity is maintained, and the subsequent muscle strength intensity evaluation is performed. If the current heart rate intensity HR(t) is higher than $HRR_0$+D %, the heart rate intensity of the user is too high, and in such a case, the exercise intensity may be decreased to restore the heart rate to the normal range. If the current heart rate intensity HR(t) is lower than $HRR_0$−D %, the heart rate intensity of the user is too low, and in such a case, the exercise intensity may be increased to raise the heart rate to the normal range so as to ensure the exercise effectiveness.

Returning to the flowchart of FIG. 5, in Step S506, the computing device 16 determines whether the monitored current heart rate is higher than the heart rate reference value. If the current heart rate is higher than the heart rate reference value, the procedure proceeds to Step S514, and the computing device 16 decreases the exercise intensity.

However, if the current heart rate is not higher than the heart rate reference value, the procedure proceeds to Step S508, and the computing device 16 uses the biophysical quantity sensor 12 to monitor the current muscle strength of each muscle portion when the user performs the exercise. In Step S510, the computing device 16 accesses the exercise history of the user from the storage device 14 to obtain the muscle strength reference value of the muscle portion when the user previously performed the exercise. Steps S508 and S510 are the same as or similar to Steps S202 and S204 in the previous embodiment, and therefore descriptions thereof are not repeated hereinafter.

In Step S512, the computing device 16 compares the current muscle strength with the muscle strength reference value to determine how to adjust the exercise intensity. If the current muscle strength is lower than the muscle strength reference value, in Step S514, the computing device 16 determines that the muscle strength intensity declines, and accordingly decreases the exercise intensity for the muscle of the user to rest and avoid exercise injuries. If the current muscle strength is equal to the muscle strength reference value, in Step S516, the computing device 16 determines that the muscle strength intensity is unchanged and maintains the current exercise intensity. If the current muscle strength is higher than the muscle strength reference value, in Step S518, the computing device 16 determines that the muscle strength intensity increases, and accordingly increases the exercise intensity for the muscle strength of the user to grow continuously. In an embodiment, for example, the computing device 16 sets a tolerance range centered on the muscle strength reference value. If the current muscle strength falls within the tolerance range, the current muscle strength is considered to be equal to the muscle strength reference value, and the exercise intensity is not adjusted. That is, the current muscle strength is considered to be higher or lower than the muscle strength reference value only when the current muscle strength exceeds the tolerance range, and then the exercise intensity is adjusted.

In the present embodiment, the above method combines heart rate sensing with muscle strength intensity sensing to evaluate the heart rate and muscle strength of the user during the exercise, so as to instantly adjust the exercise intensity, thereby improving the exercise effectiveness and avoiding exercise injuries.

In addition to the heart rate and muscle strength intensity evaluations described above, in an embodiment of the disclosure, the equivalent conversion between machines on condition of same exercise intensity is further calculated on multiple combinations of machines and the training amounts thereof, so as to equivalently convert the menu (or adjusted menu) of the current exercise to another machine pursuant to the user's needs (for example, adjustment of the exercise intensity), and instruct the user to implement the converted menu using a substitute machine to continue the previous exercise.

After the exercise intensity of the user's exercise is adjusted according to the above embodiment, in an embodiment of the disclosure, for example, a current muscle exertion total work $P_A$ of the current machine under the adjusted exercise intensity and a substitute muscle exertion total work $P_B$ of a substitute machine under this exercise intensity in one cycle are further calculated. A ratio obtained by dividing the current muscle exertion total work by the substitute muscle exertion total work of the substitute machine may be used as a conversion factor T under the same exercise intensity. Then, the training amount of the new menu is the total training amount of the original exercise menu multiplied by the conversion factor T. The formula is as follows.

$$T = P_A / P_B$$

By displaying the converted menu (which may be multiple sets of converted menus corresponding to different substitute machines) on the prompt device (not shown), the user may be prompted to select and change the machine.

Figure 7:
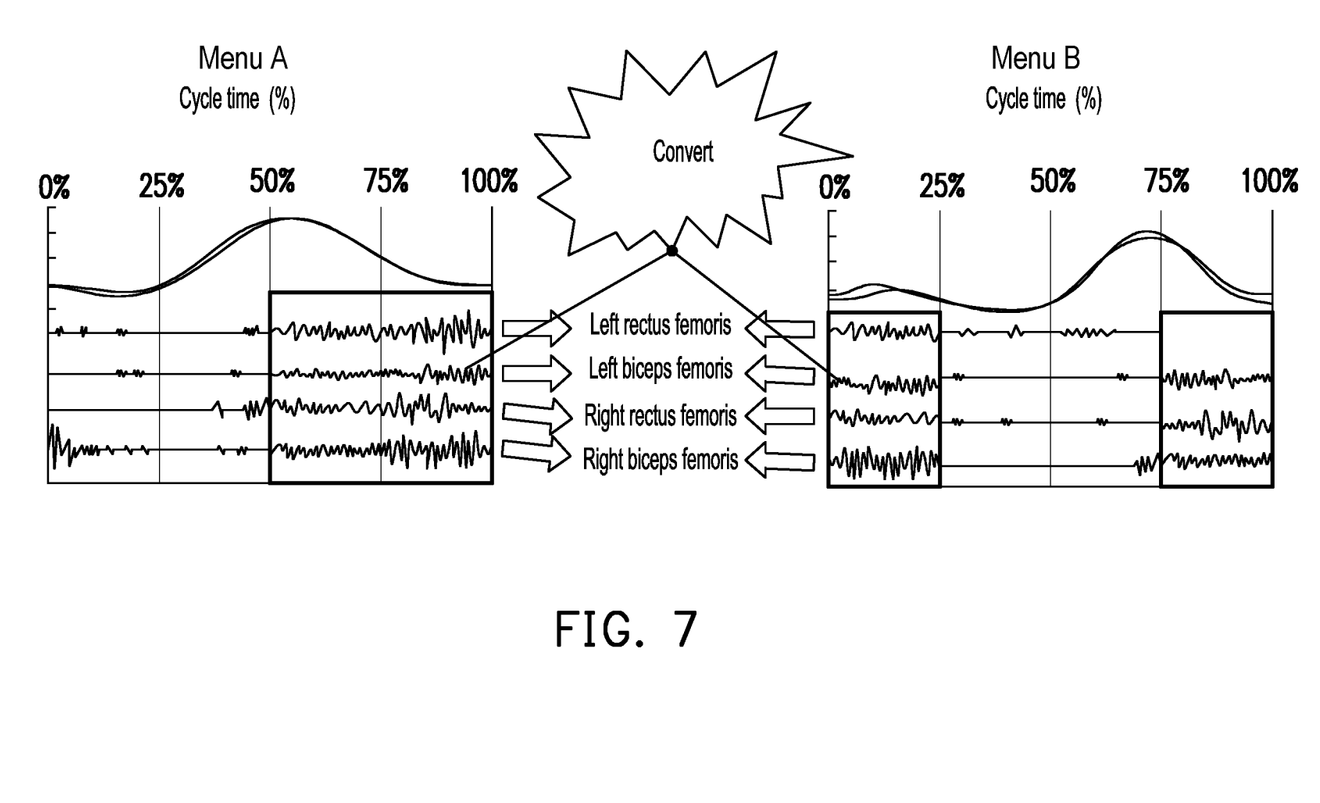
FIG. 7 is a diagram of equivalent conversion between exercise menus according to an embodiment of the disclosure.

For example, FIG. 7 is a diagram of equivalent conversion between exercise menus according to an embodiment of the disclosure. Referring to FIG. 7, the present embodiment illustrates a process of conversion from a menu A to a menu B. The figure on the left shows the muscle strength curves sensed by the EMG sensors disposed on the left rectus femoris, left biceps femoris, right rectus femoris, and right biceps femoris when the user exercises following the menu A (using the current machine). The figure on the right shows the muscle strength curves sensed by the EMG sensors disposed on the left rectus femoris, left biceps femoris, right rectus femoris, and right biceps femoris when the user exercises following the menu B (using the substitute machine). By calculating the muscle exertion total work sensed on each muscle when the user exercises following the menus A and B, and calculating the ratio to the muscle exertion total work corresponding to the same muscle, the training amount required after menu conversion is obtained.

According to the present embodiment, the method described above not only helps the user adjust the exercise intensity during the exercise to improve the exercise effectiveness but also equivalently converts the exercise menu to other machines according to different needs for the user to find a machine suitable for the current state and continue the exercise.

In the above embodiment, the computing device 16 of the exercise sensing system 10 is, for example, integrated in the training machine operated by the user or a wearable device (for example, smart clothes) worn by the user, so as to instantly monitor the current state of the user during the exercise, and adjust the exercise intensity (directly adjusted by the machine itself) or prompt the user to adjust the exercise intensity (displayed on the prompt device) timely. In other embodiments, the exercise sensing system 10 may be provided independently of a training machine (for example, a weight training device), and may be constructed on a computer or server of the service provider (for example, a gym operator) or constructed on a portable device such as a mobile phone of the user. By receiving sensing data through the biophysical quantity sensor worn on the user, the exercise sensing system 10 can also monitor the exercise of the user and instantly prompt the user to adjust the exercise intensity (displayed on the prompt device).

Figure 8:
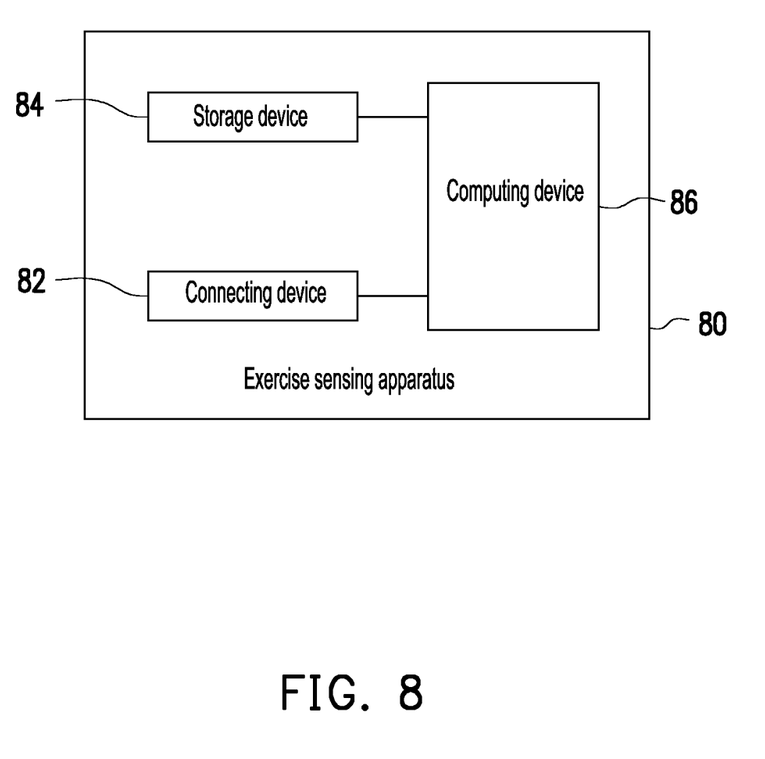
FIG. 8 is a block diagram of an exercise sensing apparatus according to an embodiment of the disclosure.

For example, FIG. 8 is a block diagram of an exercise sensing apparatus according to an embodiment of the disclosure. Referring to FIG. 8, the exercise sensing apparatus 80 of the present embodiment is, for example, a training machine such as a weight training device operated by the user, or a wearable device worn on the user. The exercise sensing apparatus 80 includes a connecting device 82, a storage device 84, and a computing device 86. The functions thereof are described below.

The connecting device 82 is, for example, connected to the biophysical quantity sensor disposed on at least one muscle portion of the user in a wired or wireless manner, so as to receive the data obtained by the biophysical quantity sensor, such as the current muscle strength of the muscle portion when the user performs the exercise. In terms of wired connection, the connecting device 82 may be a universal serial bus (USB), RS232, a universal asynchronous receiver/transmitter (UART), an internal integrated circuit (I2C), a serial peripheral interface (SPI), a display port, a thunderbolt, or a local area network (LAN) interface, but the disclosure is not limited thereto. In terms of wireless connection, the connecting device may support communication protocols such as wireless fidelity (Wi-Fi), RFID, Bluetooth, infrared, near-field communication (NFC), device-to-device (D2D), etc., but the disclosure is not limited thereto.

The storage device 84 is, for example, any type of fixed or movable random access memory (RAM), read-only memory (ROM), flash memory, hard disk, similar devices, or a combination of the foregoing and is configured to store a program to be executed by the computing device 86. In an embodiment, the storage device 84 also records the exercise history of the user.

The computing device 16 is, for example, a central processing unit (CPU), a programmable general-purpose or special-purpose microprocessor, a digital signal processor (DSP), a programmable controller, an application specific integrated circuit (ASIC), other similar devices, or a combination of the foregoing. In the present embodiment, the computing device 16 is coupled to the connecting device 82 and the storage device 84 respectively, and may receive monitoring data from the biophysical quantity sensor through the connecting device 82 and load a computer program from the storage device 84 to execute the exercise sensing method of the embodiment of the disclosure. The exercise sensing method has been described in the above embodiments, and therefore descriptions thereof are not repeated hereinafter.

In conclusion, the exercise sensing method, apparatus, and system according to the embodiments of the disclosure use sensors to sense the heart rate and muscle strength intensity of the user during exercise, and compare them with those in the exercise history, so as to instantly adjust the exercise intensity or give advice based on the current muscle strength of the user. Thereby, the user can achieve higher exercise effectiveness and avoid exercise injuries. In addition, in the embodiment of the disclosure, the exercise menu may be equivalently converted to other machines for the user to switch to an appropriate machine and continue the exercise.

Although the disclosure has been described with reference to the above embodiments, the embodiments are not intended to limit the disclosure. A person of ordinary skill in the art may make variations and modifications without departing from the spirit and scope of the disclosure. Therefore, the protection scope of the disclosure should be subject to the appended claims.

What is claimed is:

1. An exercise sensing method adapted for an exercise sensing system comprising a computing device and at least one biophysical quantity sensor, which is disposed on at least one muscle portion of a user, the exercise sensing method comprising:
   monitoring an EMG signal of the at least one muscle portion when the user performs an exercise with the at least one biophysical quantity sensor;
   calculating an average signal of the EMG signal for a complete cycle to obtain a muscle strength corresponding to the at least one muscle portion;
   obtaining a muscle strength curve according to the muscle strength, and calculating a peak value of the muscle strength curve as a current muscle strength of the at least one muscle portion;
   accessing an exercise history of the user to obtain a muscle strength reference value of the at least one muscle portion when the user previously performed the exercise; and
   calculating a change percentage of the current muscle strength relative to the muscle strength reference value to compare the current muscle strength with the muscle strength reference value, and adjusting a menu of the exercise according to the change percentage to increase or decrease an exercise intensity of the exercise.

2. The exercise sensing method according to claim 1, wherein comparing the current muscle strength with the muscle strength reference value to adjust the exercise intensity of the exercise further comprises:
   equivalently converting an adjusted menu to a substitute machine, and instructing the user to implement a converted menu using the substitute machine, comprising:
   calculating a current muscle exertion total work of a current machine under an adjusted exercise intensity, and a substitute muscle exertion total work of the substitute machine under the exercise intensity in one cycle; and
   calculating a ratio of the current muscle exertion total work to the substitute muscle exertion total work to serve as a conversion factor under the same exercise intensity, wherein a training amount of the converted menu is a total training amount of the original menu multiplied by the conversion factor.

3. The exercise sensing method according to claim 1, wherein the exercise sensing system further comprises a heart rate sensor, and the exercise sensing method further comprises:
   monitoring a current heart rate when the user performs the exercise with the heart rate sensor;
   accessing the exercise history of the user to obtain a heart rate reference value when the user previously performed the exercise; and
   comparing the current heart rate with the heart rate reference value to adjust the exercise intensity of the exercise or suspend the user from performing the exercise.

4. The exercise sensing method according to claim 1, further comprising:
   recording the current muscle strength in the exercise history to serve as the muscle strength reference value.

5. An exercise sensing system, comprising:
   at least one biophysical quantity sensor disposed on at least one muscle portion of a user to sense a force exerted by the at least one muscle portion;
   a storage device recording an exercise history of the user; and
   a computing device coupled to the at least one biophysical quantity sensor and the storage device, and configured to:
   monitor an EMG signal of the at least one muscle portion when the user performs an exercise with the at least one biophysical quantity sensor;
   calculate an average signal of the EMG signal for a complete cycle to obtain a muscle strength corresponding to the at least one muscle portion;
   monitor a current muscle strength of the at least one muscle portion;
   monitor the muscle strength to obtain a muscle strength curve, and calculate a peak value of the muscle strength curve as a current muscle strength of the at least one muscle portion;
   access the exercise history of the user from the storage device to obtain a muscle strength reference value of the at least one muscle portion when the user previously performed the exercise; and calculate a change percentage of the current muscle strength relative to the muscle strength reference value to compare the current muscle strength with the muscle strength reference value, and adjust a menu of the exercise according to the change percentage to increase or decrease an exercise intensity of the exercise.

6. The exercise sensing system according to claim 5, wherein the computing device further equivalently converts an adjusted menu to a substitute machine, and instructs the user to implement a converted menu using the substitute machine, comprising: calculating a current muscle exertion total work of a current machine under an adjusted exercise intensity and a substitute muscle exertion total work of the substitute machine under the exercise intensity in one cycle, and calculating a ratio of the current muscle exertion total work to the substitute muscle exertion total work to serve as a conversion factor under the same exercise intensity, wherein a training amount of the converted menu is a total training amount of the original menu multiplied by the conversion factor.

7. The exercise sensing system according to claim 5, wherein the computing device further comprises a heart rate sensor, and the computing device further monitors a current heart rate when the user performs the exercise with the heart rate sensor, accesses the exercise history of the user to obtain a heart rate reference value when the user previously performed the exercise, and compares the current heart rate with the heart rate reference value to adjust the exercise intensity of the exercise or suspend the user from performing the exercise.

8. The exercise sensing system according to claim 5, wherein the computing device further records the current muscle strength in the exercise history in the storage device to serve as the muscle strength reference value.

9. An exercise sensing apparatus, comprising:
a connecting device receiving a force exerted by at least one muscle portion of a user monitored by at least one biophysical quantity sensor disposed on the at least one muscle portion;
a storage device recording an exercise history of the user; and
a computing device coupled to the connecting device and the storage device, and configured to:
receive an EMG signal corresponding to the force exerted by the at least one muscle portion monitored by the at least one biophysical quantity sensor when the user performs an exercise with the connecting device;
calculate an average signal of the EMG signal for a complete cycle to obtain a muscle strength corresponding to the force exerted by the at least one muscle portion;
obtain a muscle strength curve according to the muscle strength, and calculate a peak value of the muscle strength curve as a current muscle strength of the at least one muscle portion;
access the exercise history of the user from the storage device to obtain a muscle strength reference value of the at least one muscle portion when the user previously performed the exercise; and
calculate a change percentage of the current muscle strength relative to the muscle strength reference value to compare the current muscle strength with the muscle strength reference value to adjust, and adjust a menu of the exercise according to the change percentage to increase or decrease an exercise intensity of the exercise.

10. The exercise sensing apparatus according to claim 9, wherein the computing device further equivalently converts an adjusted menu to a substitute machine, and instructs the user to implement a converted menu using the substitute machine, comprising: calculating a current muscle exertion total work of a current machine under an adjusted exercise intensity and a substitute muscle exertion total work of the substitute machine under the exercise intensity in one cycle, and calculating a ratio of the current muscle exertion total work to the substitute muscle exertion total work to serve as a conversion factor under the same exercise intensity, wherein a training amount of the converted menu is a total training amount of the original menu multiplied by the conversion factor.

11. The exercise sensing apparatus according to claim 9, wherein the computing device further receives a current heart rate monitored by a heart rate sensor when the user performs the exercise with the connecting device, accesses the exercise history of the user from the storage device to obtain a heart rate reference value when the user previously performed the exercise, and compares the current heart rate with the heart rate reference value to adjust the exercise intensity of the exercise or suspend the user from performing the exercise.

12. The exercise sensing apparatus according to claim 9, wherein the computing device further records the current muscle strength in the exercise history in the storage device to serve as the muscle strength reference value.

\* \* \* \* \*